United States Patent [19]
Amiot

[11] Patent Number: 5,416,022
[45] Date of Patent: * May 16, 1995

[54] CELL CULTURE APPARATUS

[75] Inventor: Bruce P. Amiot, Roseville, Minn.

[73] Assignee: Cellex Biosciences, Inc., Minneapolis, Minn.

[*] Notice: The portion of the term of this patent subsequent to Jan. 7, 2009 has been disclaimed.

[21] Appl. No.: 143,385

[22] Filed: Oct. 29, 1993

Related U.S. Application Data

[63] Continuation of Ser. No. 717,600, Jun. 19, 1991, abandoned, which is a continuation-in-part of Ser. No. 230,400, Aug. 10, 1988, Pat. No. 5,079,168.

[51] Int. Cl.$^6$ .................................................. C12M 3/06
[52] U.S. Cl. .................................. 435/284; 435/311; 435/313
[58] Field of Search ............... 435/240.2, 240.241, 435/240.242, 240.23, 240.25, 284–286, 288, 299–301, 311, 313–316; 210/321.64, 321.72, 321.75, 321.76, 321.79, 321.8, 321.84, 321.85, 321.88, 321.89; 261/122, DIG. 48; 422/48

[56] References Cited

U.S. PATENT DOCUMENTS

| | | | |
|---|---|---|---|
| 3,060,934 | 10/1962 | Claffe et al. | 210/321.75 |
| 3,212,498 | 10/1965 | McKirdy et al. | 210/321.75 |
| 3,458,048 | 7/1969 | Swenson | 210/321.75 |
| 3,796,313 | 3/1974 | Bigt et al. | 210/321.75 |
| 3,941,662 | 3/1976 | Munder et al. | 195/127 |
| 4,225,671 | 9/1980 | Puchinger et al. | 435/285 |
| 4,391,912 | 7/1983 | Yoshida et al. | 435/284 |
| 4,661,455 | 4/1987 | Hubbard | 435/285 |
| 4,937,196 | 6/1990 | Wrasidlo et al. | 435/284 |
| 5,079,168 | 1/1992 | Amiot | 435/284 |

FOREIGN PATENT DOCUMENTS

232975 8/1987 European Pat. Off. .
419234 3/1991 European Pat. Off. .

Primary Examiner—William H. Beisner
Attorney, Agent, or Firm—Sughrue, Mion, Zinn, Macpeak & Seas

[57] ABSTRACT

A compact, easily assembled cell culturing device comprising at least one cell culturing envelope, the interior of which defines a cell culturing space. The cell culturing envelope is retained within a pair of rigid plates having various reliefs which, in turn, form cavities when the plates are placed together. The cell culturing envelope includes a plurality of hollow fibers disposed in the culturing space formed between upper and lower membrane sheets which are sealed together. Tubes communicate with the culturing space. Accordingly, greater amounts of oxygen are provided to the cells at a faster rate to produce cells and/or cell products more economically and in higher yield.

14 Claims, 6 Drawing Sheets

CELL CULTURE APPARATUS

CROSS REFERENCE TO RELATED APPLICATIONS

This is a continuation of U.S. application Ser. No. 07/717,600, filed Jun. 19, 1991, now abandoned, which is a continuation-in-part of U.S. application Ser. No. 07/230,400, filed Aug. 10, 1988, now U.S. Pat. No. 5,079,168.

FIELD OF THE INVENTION

This invention relates to a device for cultivating cells in vitro. More particularly, it relates to a compact, easily assembled cell culturing device comprising at least one envelope, the interior of which defines a cell culturing space. The invention relates even more particularly to a cell culturing device, simple in design, yet which provides for efficient gas delivery and removal to and from the cell culturing space to be separate from nutrient media delivery and removal whereby greater amounts of oxygen are provided to the cells at a faster rate to produce cells and/or cell products more economically and in higher yield.

BACKGROUND OF THE INVENTION

The culturing of living cells in vitro is performed for a variety of purposes, including the preparation of viral vaccines, the recovery of valuable by-products of cell metabolism and the production of tissue-like derivatives for creating artificial organs.

Several problems are associated with growing living cells in vitro to produce dense masses of cells. First, individual components of the nutrient medium must diffuse through the cell layers to reach all cells. This becomes increasingly difficult as the thickness of the cell layer increases.

Second, the maintenance of a suitable environment for cell growth is difficult because the fluid immediately adjacent a growing cell is continuously changing as cellular metabolism proceeds and is returned to its original status only in stepwise fashion when the nutrient medium is changed or agitated en masse.

Third, a lattice or suitable material upon which to grow some types of cells is required.

Various types of apparatus and methods have been developed in response to these needs. One method involves attaching and growing cells on the interior surface of plastic or glass roller tubes and bottles as disclosed in U.S. Pat. No. 3,450,598. Another method involves attaching the cells to a flat surface of stationary containers such as petri dishes or rectangularly shaped culture plates. The flat surfaces can be stacked one on top of each other in a spaced-apart array as disclosed in U.S. Pat. No. 3,843,454.

The use of hollow fibers or synthetic capillaries has more recently been disclosed as a support matrix for the propagation of cells. For example, U.S. Pat. Nos. 3,821,087; 3,883,393; 4,184,922; 4,200,689; 4,206,015 and 4,220,725, all to Knazek et al, variously disclose apparatus and methods for the in vitro growth of cells on semi-permeable, tubular membranes or capillaries wherein cells are initially allowed to settle onto the outer surfaces of the capillary walls in a nutrient medium. Nutrients diffuse from the perfusing medium through the capillary walls and are utilized by the cells. Cell products diffuse from the cells, through the capillary walls and into the perfusate, from which cell products may be recovered.

U.S. Pat. Nos. 4,184,922 and 4,200,689 disclose cell culturing devices comprising a single bundle of fibers wherein some of the fibers are connected to one perfusion circuit and the remaining fibers are connected to a second perfusion circuit. The difference in pressure between the two circuits produces convective currents of perfusate within the extracapillary space and thereby improves nutrient distribution to the growing cells.

In U.S. Pat. No. 4,220,725, a bundle of capillaries, upon which cells are allowed to grow, is wrapped in a porous envelope or sheet material which creates an extra-envelope space into which the cells can migrate for periodic removal without disturbing the main cell culture. The creation of the extra-envelope space increases the surface area for nutrient end waste product diffusion to and from the cells located on the outer surface of the capillaries.

In U.S. Pat. No. 3,997,396, cells are attached to and grown on one side or surface of a single hollow fiber membrane wherein the cells are propagated and maintained by passing oxygen through the membrane from the side opposite that to which the cells are attached and into contact with the cells while simultaneously incubating the cells in a nutrient medium. By continuously passing oxygen through the membrane from the side opposite that on which the cells are attached, a continuous and uniform supply of oxygen reaches and nourishes the cells thereby facilitating aerobic propagation of the cells in the desired tissue densities.

In U.S. Pat. Nos. 4,087,327 and 4,201,845 to Feder et al, an in vitro cell culture reaction system is disclosed which utilizes elongate hollow or solid fibers arranged in a shallow layer configuration as a matrix for cell attachment on the outer surface of the fibers. Nutrient media flow is directed substantially uniformly through the fiber layer and substantially transverse to the plane of the elongate axes of the fibers. The cells are aerated by passing oxygen through the interior of the fibers which then permeates the fiber walls. The use of a shallow bed of fibers in a relatively short path of media flow results in a substantial reduction of the nutrient and metabolic product gradients that is normally produced by the fibrous bundle as well as a more extensive utilization of the fiber surface for cell attachment.

U.S. Pat. No. 4,391,912 discloses a device for cultivating floating animal cells comprising a gas permeable shell and a plurality of hollow fibers enclosed within the shell, wherein the hollow fibers are open at either end outside of the shell and have a pore diameter of from about 102 angstroms to $5 \times 10^4$ angstroms. Nutrient medium passes through the interior of the hollow fibers and oxygen passes through the shell and the animal cells are cultivated in the space between the shell and the hollow fibers. These pore diameters of the hollow fibers are disclosed as optimizing efficient exchange of nutrients and metabolic products produced by the cells resulting in high density cell growth.

Notwithstanding the usefulness of the hollow fiber cell culture devices, it has been found that the nutrient media flow through the hollow capillaries prevents complete penetration of the capillary bundle by the cells and sets up an undesirable gradient of medium flow. As a result, there is an incomplete utilization of the available capillary surface for cell attachments and cells become unevenly distributed along the surface. Also, as the nutrient medium flows through the reactor, nutrients are more available to the cells near the inlet, and as the medium flows to the outlet, metabolic products such as lactic acid accumulate in the medium, undesirably affecting pH and producing other toxic effects on the cells.

Another significant difficulty encountered with these hollow fiber-type cell culture devices concerns the high media circulation rates necessary to supply adequate oxygen to the cells. Specifically, aqueous nutrient media, equilibrated with air, is able to carry 4.5 ml of oxygen per liter (37° C., 760 mm of Hg). This relative inability of aqueous solutions to carry oxygen causes the rate at which oxygen is supplied to the cells to be the limiting step in in vitro cell growth operations. In order to produce high yields of cells and/or cell secreted products, media circulation rates must be increased to provide more oxygen to cells. High circulation rates in turn cause high internal pressure and turbulence which has presented problems in terms of constructing the device on an industrial scale and in propagating mammalian cells whose sensitivity and fragility prohibit the use of too vigorous aeration and/or agitation. Vigorous aeration also causes the denaturation of many biologically and medicinally useful proteins produced by cell cultures.

Moreover, the above-described hollow fiber-type devices which provide for separate oxygen and nutrient media delivery to cells suffer from the additional disadvantages of being mechanically complex, difficult to assemble and being unduly large. Moreover, the dimensions of these devices are not constrained to maintain the growing cells in close proximity to the nutrient media supply source thus causing undesirable nutrient gradients.

Therefore, it has been desirable to provide new cell culturing devices for growing cells in vitro, particularly mammalian cells, which overcome the various difficulties associated with the prior art devices and produce cells and/or cell secreted products more economically and in higher yields.

SUMMARY OF THE INVENTION

It is thus an object of the present invention to provide an improved cell culturing device which overcomes the above-mentioned difficulties associated with the prior art.

It is another object of the present invention to provide a cell culturing device for in vitro cell propagation which features optimally efficient gas exchange between the cells and the external environment achieved by delivering and removing gas to and from the cells separately from nutrient media.

It is a further object of the present invention to provide a cell culturing device which allows for dramatically reduced nutrient media circulation rates, thereby affording greater ease in industrial scale-up.

It is an even further object of the present invention to provide a cell culturing device which is simple in design, easy to assemble, compact in size and has a gentle internal environment in which to grow cells and recover cells and/or valuable cell products in high yields.

These and other objects of the present invention are realized in a cell culture device in one embodiment comprising:

(a) at least one envelope having first and second external surfaces each having first and second lateral and longitudinal edges, wherein the envelope comprises a first membrane sheet sealed to a second membrane sheet along the first and second lateral and longitudinal edges, respectively, to define a cell culturing space therebetween, said first and second membrane sheets being porous and substantially permeable to gasses but substantially impermeable to cells and liquids;

(b) a first delivery means for delivering nutrient media to the cell culturing space;

(c) a second delivery means for delivering cells to the cell culturing space;

(d) a third delivery means for delivering gas to the cell culturing space;

(e) a first removal means for removing metabolic waste products from the cell culturing space;

(f) a second removal means for removing cells and/or cell products from the cell culturing space; and (g) a third removal means for removing gaseous waste products from the cell culturing space.

The cell culture device may further include an upper rigid plate and a lower rigid plate, which form a housing for retaining the envelope, the upper and lower rigid plates having cavities for accommodating the envelope when the upper and lower rigid plates are placed together.

The cell culturing device also may include a plurality of the envelopes being disposed between the upper and lower rigid plates. Likewise, a plurality of intermediate plates may be disposed between the upper and lower rigid plates, so that each of the envelopes is retained between a corresponding pair of plates. In addition, the upper and lower rigid plates and the intermediate plates may share a common inlet plenum and a common outlet plenum, whereby the first delivery means of each of the envelopes communicates with the common inlet plenum, and the first removal means of each of the envelopes communicates with the common outlet plenum.

BRIEF DESCRIPTION OF THE DRAWINGS

The advantages and features of the present invention will be more fully understood from the following description of the preferred embodiments, taken in conjunction with the accompanying drawings, wherein.

DETAILED DESCRIPTION OF THE PREFERRED EMBODIMENTS

In the various embodiments of the invention as illustrated in the drawings, like structures will be referred to by like reference numerals.

Figure 5:
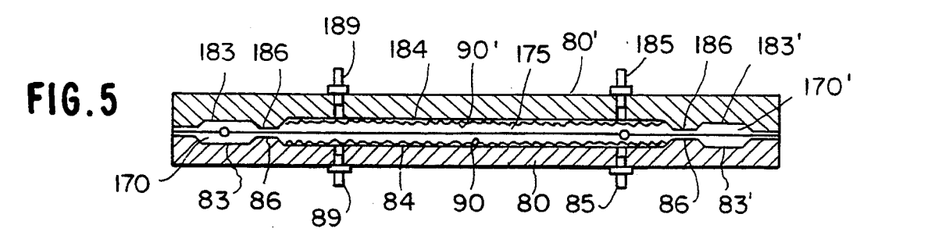
FIG. 5 is a cross-sectional view of the second basic element of the first embodiment of the present invention.
Figure 6:
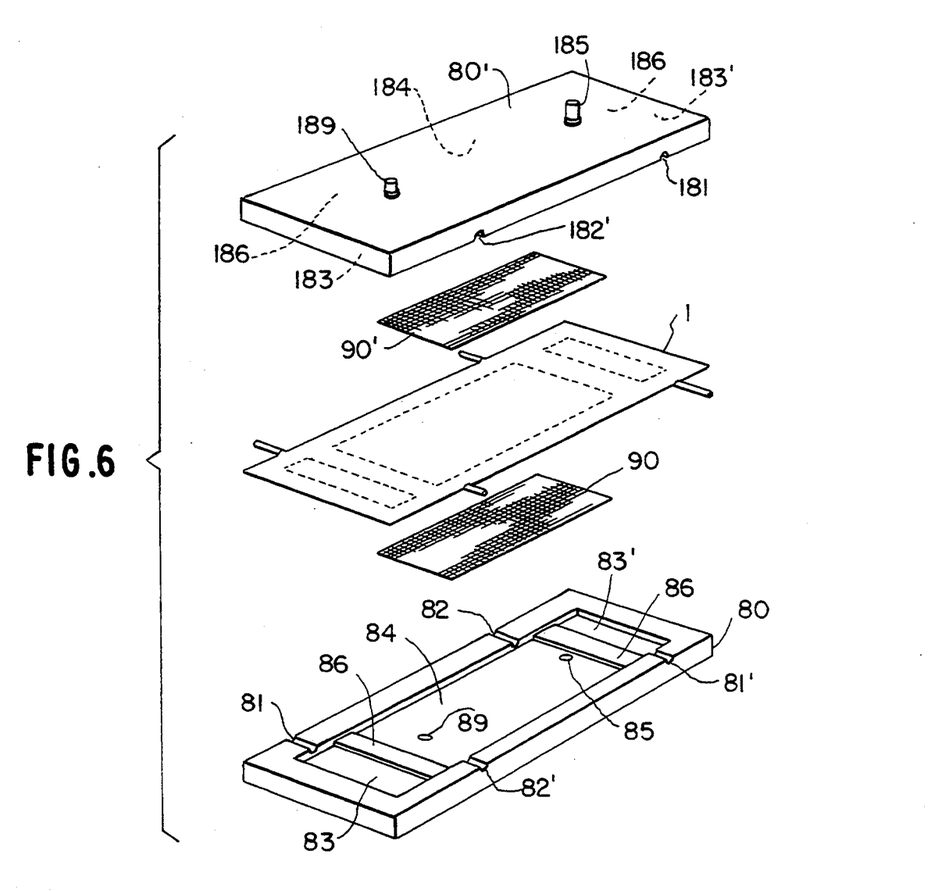
FIG. 6 is an exploded perspective view of the two basic elements of the first embodiment of the cell culturing device of the present invention showing their assembled relation to each other.
Figures 7, 8, 9:
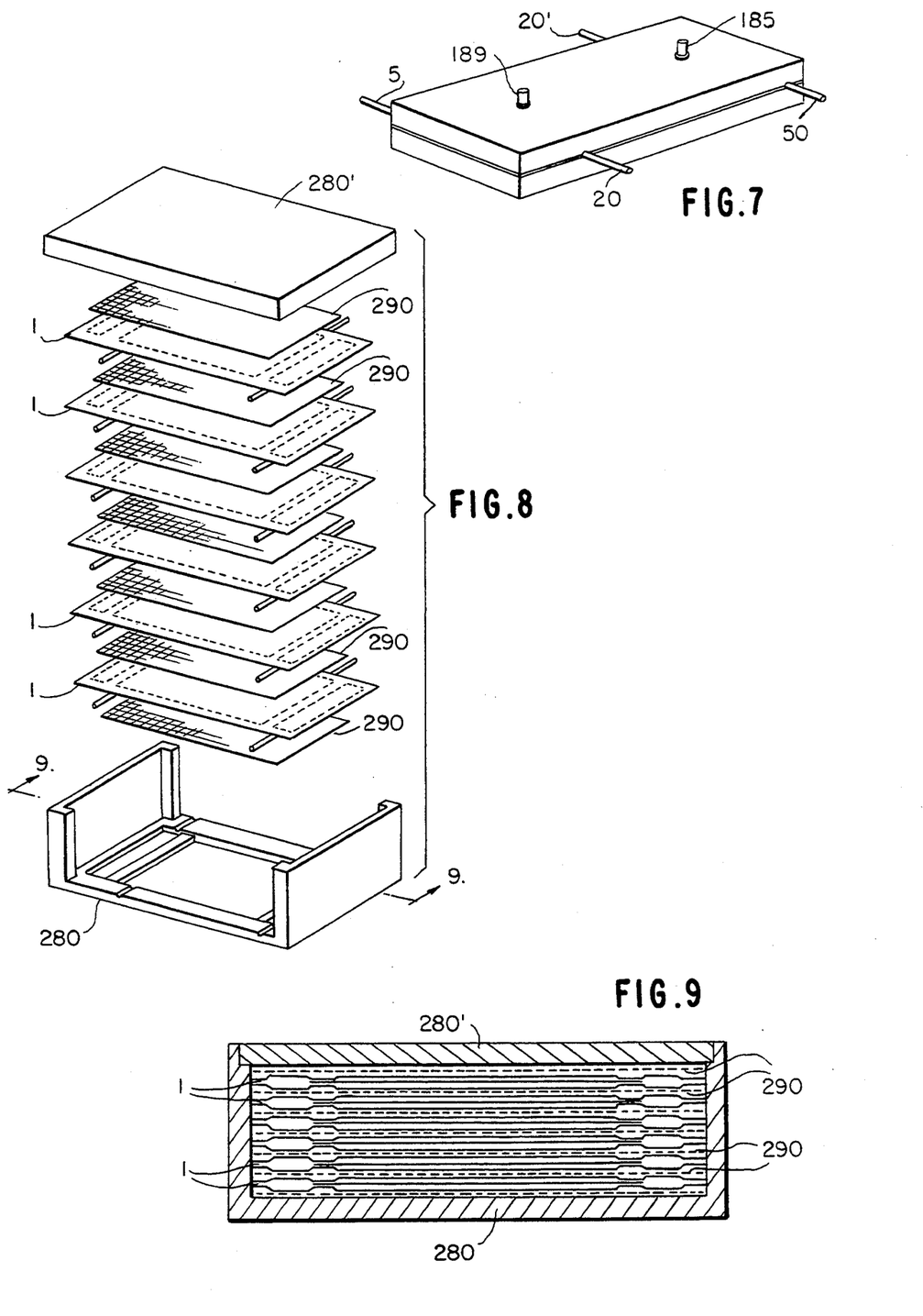
FIG. 7 is a perspective view of the first embodiment of the assembled cell culturing device of the present invention.
FIG. 8 is an exploded perspective view of a second embodiment of the cell culturing device of the present invention that incorporates a multiplicity of the first basic element of the present invention in a modified second element of the present invention.
FIG. 9 is a cross-sectional view of a second embodiment of the cell culture device of the present invention.

The first embodiment of the present invention is generally illustrated in FIGS. 1–7. The cell culture device is comprised of a cell culturing bioreactor envelope generally shown as 1 in FIG. 2 and a rigid housing generally shown in FIGS. 5 and 6. The relationship of the culturing bioreactor envelope 1 to the rigid housing is generally shown in FIG. 6 and a completed assembly of the first embodiment of this invention is shown in FIG. 7.

The construction of a culturing envelope of the first embodiment will be explained using FIG. 1 as the general reference, It is understood that the dimensions, materials and construction methods described herein are for illustrative purposes and to not in any way limit the scope of this invention.

A sheet of silicone rubber membrane 30 is trimmed to a dimension of about 125 mm wide by 200 mm long. A 3–5 mm wide bead of adhesive 65, such as medical grade silicone RTV (SILASTIC® by Dow Corning, Midland, Mich.), is applied to the entire periphery of the membrane sheet. Next, an appropriate number of hollow fibers or capillaries 40, such as CUPROPHAN®, cut to approximately the same length as the sheet membrane 30 are laid longitudinally and pressed lightly into the adhesive, one or more extra-capillary inlet and outlet tubes 20, 20' are placed on the membrane sheet such that one end of the cut end of the tube extends just past the adhesive 65 and into the area that the hollow fibers 40 are located in.

Figure 1:
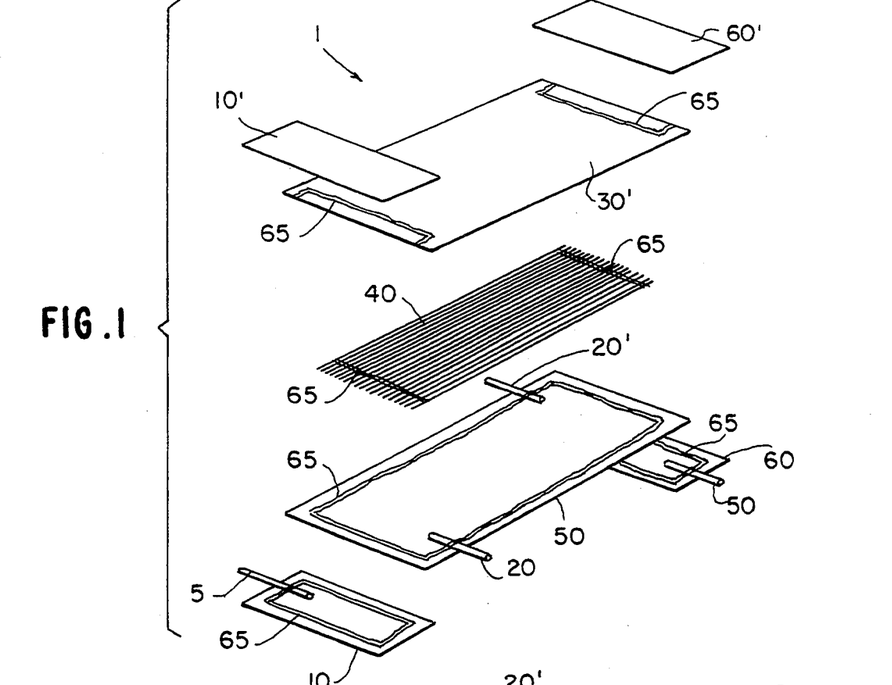
FIG. 1 is an exploded perspective view of the basic cell culturing element or bioreactor envelope according to the first embodiment of the present invention.

Secondary beads of adhesive 65 are placed across the hollow fibers 40 and the tubes 20, 20' as shown in FIG. 1. A second sheet of hydrophobic membrane 30' that is the same dimension as the first is placed over the first hydrophobic sheet 30, the hollow-fibers 40, tubes 20,20' and pressed lightly in place to thereby form a cell culturing space 75 between the membrane sheets 30,30' (see FIGS. 3 and 4). A suitable hand tool, such as a spatula or putty knife is used to press and spread the adhesive to a uniform thickness around the entire periphery thus forming the cell culturing envelope 2. An alternate method to spread the adhesive by hand, is to place the cell culturing envelope 2 between the cell culture apparatus housing plates 80, 80' that are shown in FIGS. 5 and 6 and then applying uniform pressure to the plates 80,80' to spread the adhesive to a uniform thickness.

Figure 1A:
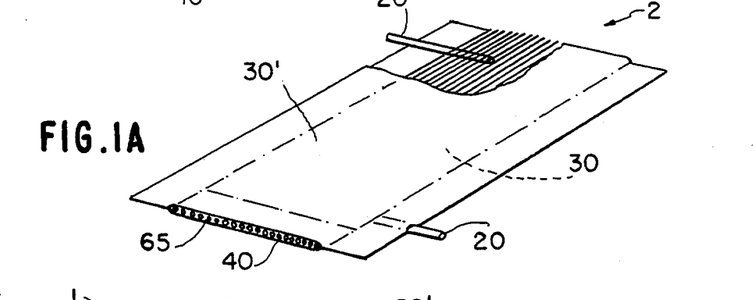
FIG. 1A is a perspective view of the basic cell culturing envelope in assembled form.
Figure 2:
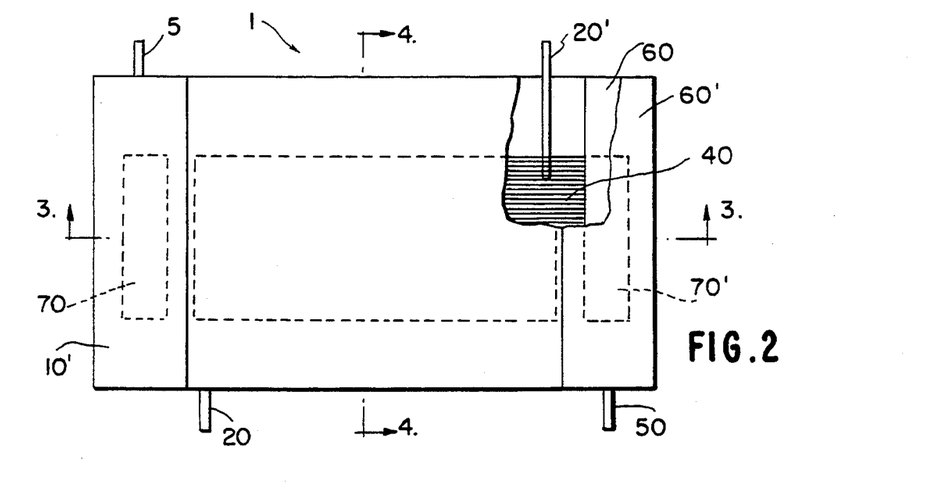
FIG. 2 is a top cut away view of the assembled basic cell culturing bioreactor envelope according to the first embodiment of the present invention.
Figure 3:
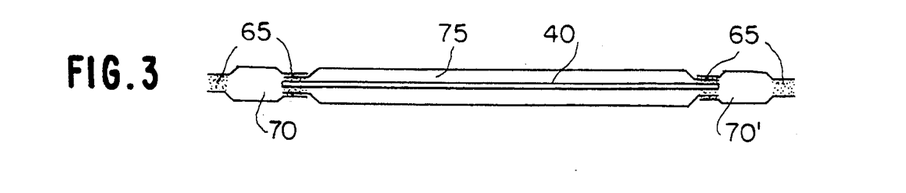
FIG. 3 is a cross-sectional view of the element of the first embodiment taken along line 3—3 in FIG. 2.
Figure 4:
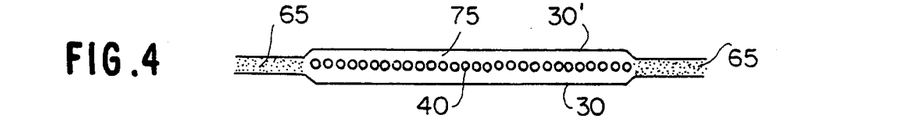
FIG. 4 is a cross-sectional view of the element of the first embodiment taken along line 4—4 in FIG. 2.

After the adhesive has cured, the lateral edges of the cell culturing envelope 2 may be trimmed to remove excess adhesive and expose the lumens of the hollow fibers 40. At this point, the cell culturing envelope 2, as shown in FIG. 1A, is ready to be used in other embodiments, such as the one shown in FIG. 8 or the medium inlet and outlet; means may be formed as detailed below in order to form a bioreactor envelope 1 as shown in FIGS. 1 and 2–4.

A medium inlet plenum 70 may be constructed by cutting 2–50 mm by 125 mm pieces 10, 10' of hydrophobic sheet membrane and adhesively affixing them to one end of the cell culturing envelope 2 in a manner similar to that used in assembling the culturing envelope 2. Briefly, a bead of adhesive is placed around the edge of the first piece of hydrophobic membrane 10 and a tube 5 of similar dimensions as before is placed across the adhesive bead as shown in FIG. 1. The previously assembled cell culture envelope 2 is placed over one of the longitudinal adhesive beads. The end of the cell culturing envelope 2 should overlap the adhesive bead by 5 to 10 mm. Secondary beads of adhesive are placed on the end of the cell culture envelope 2 and tube 5 as shown in FIG. 1 and a second piece of hydrophobic sheet membrane 10' is placed over the first. The adhesive is then pressed to a uniform thickness using the same method(s) as in the cell culture envelope 2 above.

A medium outlet plenum 70' comprised of two pieces of hydrophobic sheet membrane 60, 60' and a tube 50 may be fabricated onto the cell culture envelope 2 in the same manner as the medium inlet plenum above. Accordingly, a cell culturing bioreactor envelope 1 is formed. This cell culturing bioreactor envelope 1 may be utilized as it is as a cell culturing device. The cell culturing bioreactor envelope 1 may be assembled into a simple perfusion circuit comprised of a medium reservoir appropriately connected to a peristaltic pump (not shown), a medium inlet conduit connected between the peristaltic pump and the medium inlet tube 5 and a medium outlet conduit connecting the medium outlet tube 50 back to the medium reservoir. The entire sterilized assembly may be placed in a $CO_2$ incubator for temperature control, pH control and convective oxygen delivery. Cells may be introduced into the cell culture space 75 via the extra-capillary access/inlet tube 20 using a syringe or other appropriate device and cells and/or cell secreted products may be removed via the extracapillary access/outlet tube 20'.

As previously mentioned, the second component of the first, preferred embodiment are two rigid plates 80, 80' that retain the cell culturing bioreactor envelope 1 and define its geometry. FIG. 5 provides a cross sectional view of the plates 80 and 80' and FIG. 6 provides a detailed perspective view of one plate 80. The plates may be constructed from a variety of materials including steel, aluminum or a variety of rigid plastics such as acrylic, polycarbonate or polysulfone.

FIG. 5 is a cross sectional view of the plates 80 and 80' and shows the various reliefs formed in the plates and the cavities that the reliefs form when the plates are placed together. The cavity marked 170 retains the medium inlet plenum 70, the ridges 86, 186 retain the cell culture bioreactor envelope 1 and along with the longitudinal edges of the plates, form a gas tight compression seal against the cell culture bioreactor envelope 1. The upper plate 80' includes a medium inlet plenum relief 183 and a medium outlet plenum relief 183'. The lower plate 80 includes a medium inlet plenum relief 83 and a medium outlet plenum 83'. Plastic meshes 90, 90' provide space for gasses to flow over the surface of the cell culture envelope 2 for gas exchange and pH control. Four ports 85, 89 and 185 and 189, two in each plate and located at opposite ends of each plate, allow entry of the gasses. The cell culture envelope cavity 175 formed by reliefs 84 and 184 is where the hollow-fiber 40 containing portion of the cell culture bioreactor envelope 1 resides. The cavity shown generally at 170' houses the medium outlet plenum 70'.

FIG. 6 generally shows the relationship of the cell culture bioreactor envelope 1, plastic meshes 90, 90' and rigid plates 80, 80' The upper rigid plate 80' is a mirror image of the lower rigid plate 80. The lower plate 80 includes a medium inlet means relief 81, a medium outlet means relief 81' an extra-capillary access/inlet means relief 82' and an extra-capillary access/outlet means relief 82. The reliefs 181 and 182' on upper plate 80' correspond respectively to reliefs 81' and 82' with the other reliefs not visible in FIG. 6. The depth of the reliefs 84 and 184 control the spacing of the gas exchange membranes forming the culture envelope 2. Several different plates have been constructed so that the gas exchange membrane may be varied for experimental purposes. Membrane spacings of 65 microns to 2,000 microns distance may be achieved, with 225 to 1000 microns being the preferred spacing.

FIG. 7 shows the fully assembled first embodiment of the cell culture apparatus. A medium inlet tube 5 extra-capillary inlet tube 20, extra-capillary outlet tube 20' medium outlet 50, gas inlet 185 and gas outlet 189 are shown. The basic operation of the apparatus can be explained using this embodiment.

A medium reservoir and medium supply pump are connected to the medium inlet tube 5 of a sterile cell culture apparatus. To the medium outlet tube 50 is connected an appropriate sterile conduit containing a pH probe that can be used to monitor the pH of the medium exiting the bioreactor. pH control can be established by connecting the pH probe output to an appropriate gas proportioning control system that can adjust the $CO_2$ content of the gas stream being fed to the bioreactor via the gas inlet 185. Cells can be introduced into the extra-capillary space of the bioreactor via the extra-capillary inlet tube 20. Cells and/or cell secreted products may be harvested from either extra-capillary access tube 20, 20' or appropriate conduits, pumps and reservoirs may be attached to continuously or intermittently provide fresh nutrients and/or supplements to the extra-capillary space and continuously or intermittently harvest cells and/or cell secreted products from the extra-capillary space.

EXAMPLE 1

A cell culture apparatus of the first embodiment was substituted for the hollow-fiber bioreactor and gas exchanger in an ACUSYST-Jr ® (Endotronics, Inc., Minneapolis, Minn.) flowpath and a cell culture was conducted following the general operating instructions that accompany the instrument.

The cell culturing envelope was of the approximate size as described earlier and the bioreactor rigid plates were machined so that the hydrophobic membrane spacing was about 250 microns. The culturing envelope contained 127 CUPROPHAN hollow fibers and had an extra-capillary volume of about 1.8 ml.

A murine hybridoma that secretes an Ig G antibody was used. The operating parameters were temperature 37° C., pH 7.30, glucose concentration 150 mg % minimum, and lactate concentration 150 mg % maximum. Approximately $2 \times 10^7$ viable cells were inoculated into the extra-capillary space of the bioreactor.

The cells were cultured for about 30 days and then the experiment was terminated. At the end of the experiment the average metabolic activity and production rate of the bioreactor of the present invention was compared to the average rates from previous experiments (n=6) that used the conventional hollow-fiber bioreactor. The results are summarized in the table below:

|  | Glucose Consumption (mg per ml of bioreactor per hour) | Ig G Production (mg per ml of bioreactor per day) |
| --- | --- | --- |
| Present Invention | 17.06 mg/ml/hr. | 15.82 mg/ml/day |
| ACUSYST-Jr | 4.38 mg/ml/hr. | 6.58 mg/ml/day |

An alternative embodiment of the present invention is shown in FIGS. 8 and 9. In this embodiment numerous cell culture bioreactor envelopes 1 are incorporated into a single rigid housing comprised of a lower 280 and an upper 280' component. The individual bioreactor envelopes 1 with plastic mesh 290 between them would be constrained between the two rigid components which are fastened to each other in an appropriate manner. The various inlet and outlet means of the individual cell culture bioreactor envelopes 1 may be connected to individual delivery means and conduits or each similar inlet and outlet could be manifolded together in parallel.

Figures 10, 11, 12:
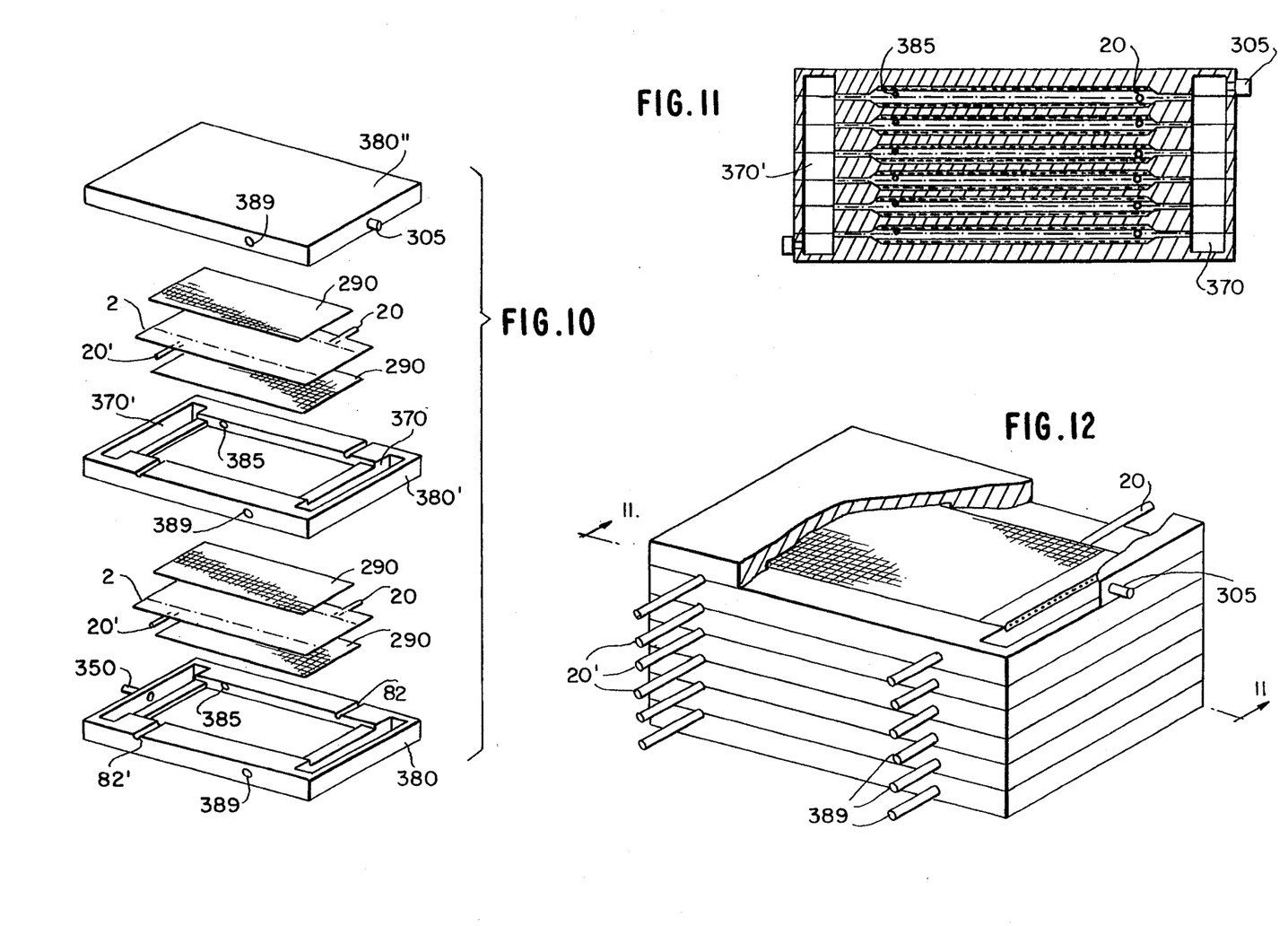
FIG. 10 is an exploded perspective view of a third embodiment of the present invention in which the first nutrient media delivering means of each first basic cell culturing envelopes are fed by a common nutrient delivery plenum and the first removal means for removing metabolic waste products are similarly in communication with a common waste removal plenum (two envelopes are shown)
FIG. 11 is a cross-sectional view of the assembled third embodiment of the cell culturing device of the present invention and showing multiple envelopes.
FIG. 12 is a cut-away perspective view of a third embodiment of the present invention.

Yet another embodiment of the current invention is shown in FIGS. 10–12. In this version, the cell culture envelope 2 of the first embodiment would be constructed without the medium inlet plenum 70 and medium outlet plenum 70'. A common medium inlet plenum 370 (FIG. 11) having medium inlet 305 and a common medium outlet plenum 370' (FIG. 11) having medium outlet 350 are formed when a number of culture envelopes 2 are assembled into the multi-pieced rigid housing 380, 380' and 380''. The extra-capillary access means or tubes 20, 20' and the gassing means 385, 389 may be manifolded in parallel or operated separately as in the previous embodiment.

Figure 13:
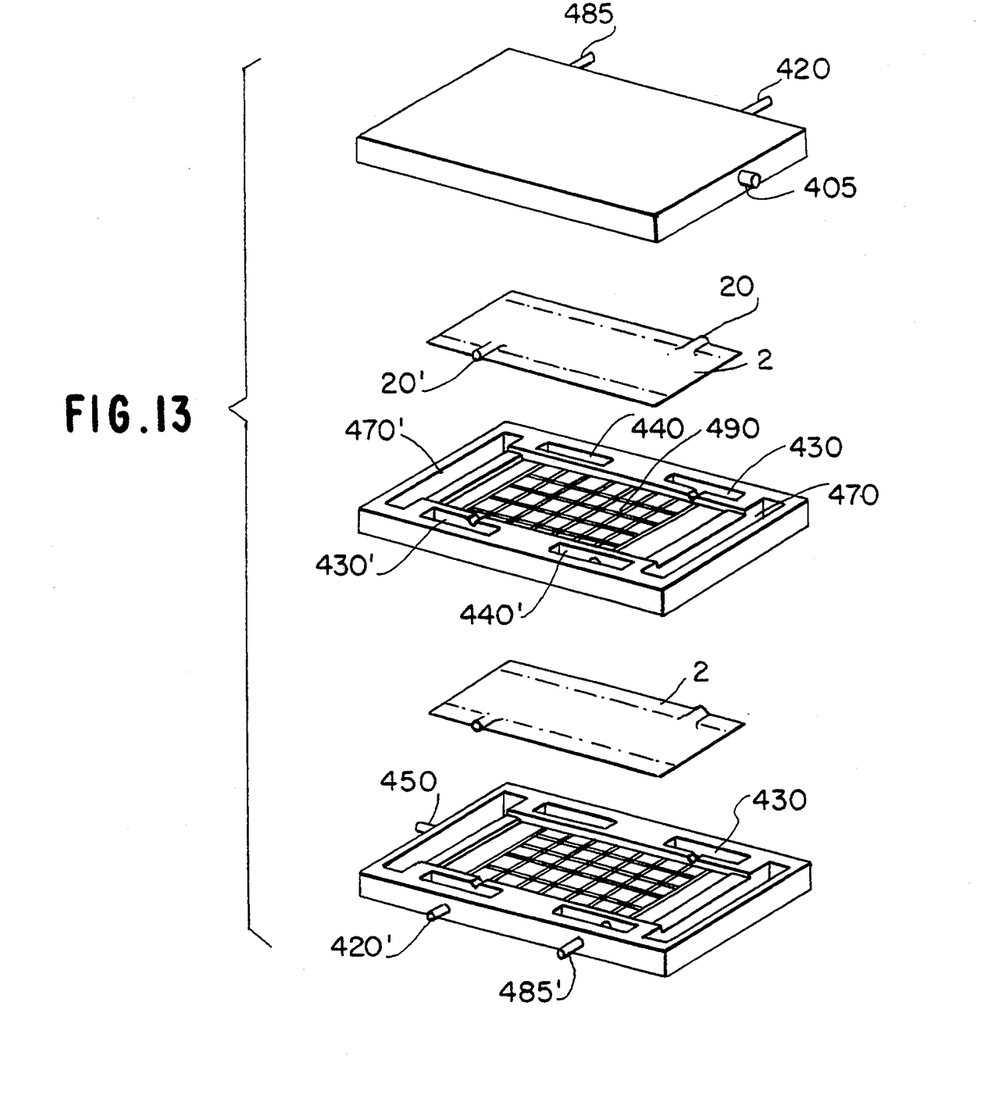
FIG. 13 is an exploded perspective view of a fourth embodiment of the present invention in which each respective delivery means (nutrient media, cells, gas) of each basic cell culturing element is fed by common plenums and each respective removal means (metabolic waste, cells and/or cell products, gaseous waste) are connected to common removal plenums (two envelopes are shown)
Figure 14:
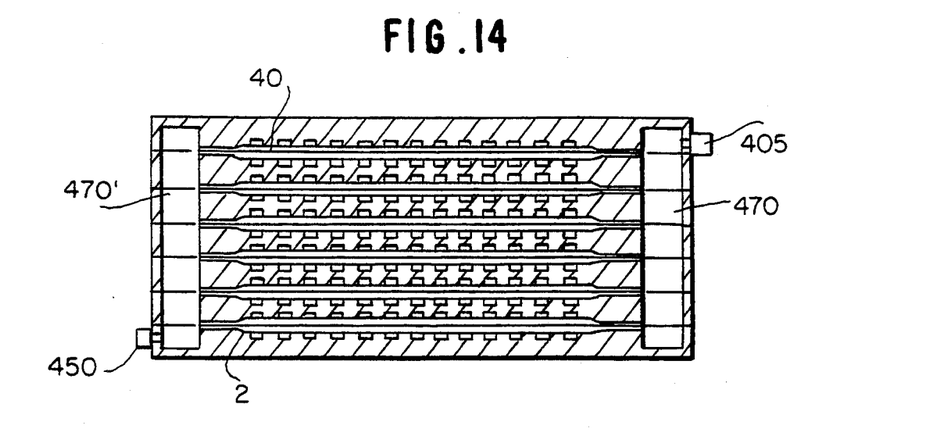
FIG. 14 is a fragmentary perspective view of the fourth embodiment of the cell culture device of the present invention and showing multiple envelopes.
Figure 15:
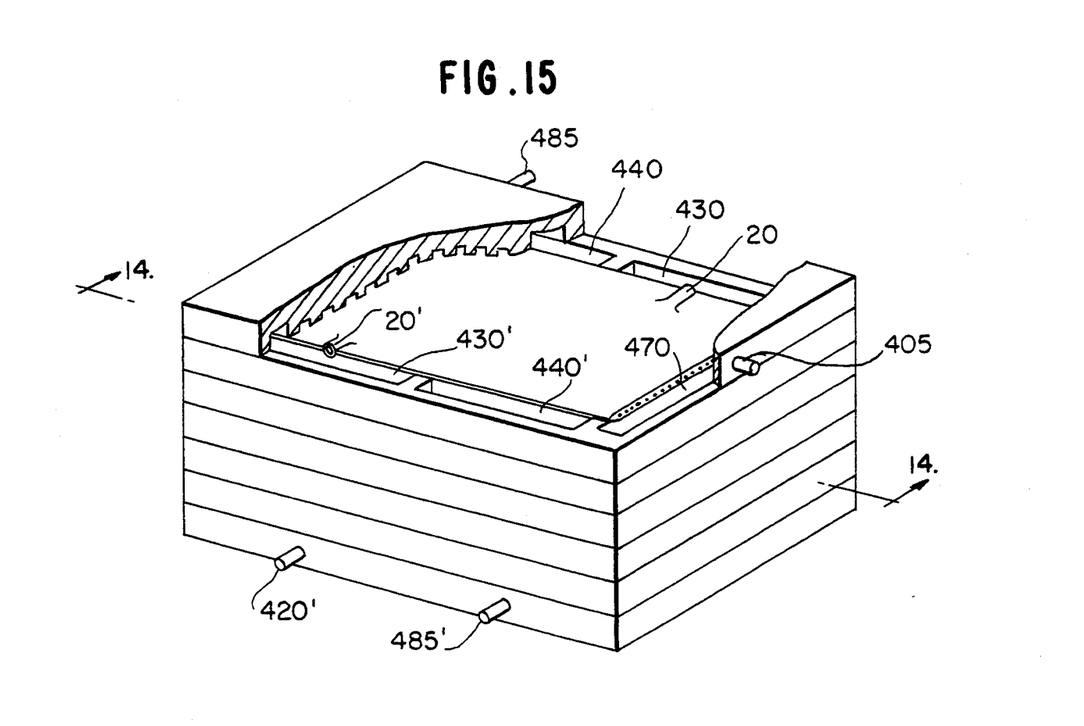
FIG. 15 is a cut-away perspective view of the fourth embodiment of the assembled cell culture device of the present invention.

A fourth embodiment is shown in FIGS. 13–15. In this embodiment, cell culturing envelopes 2 similar to the previous embodiment are used to construct a multi-part rigidly housed cell culturing apparatus. In this configuration, each similar inlet and outlet means on each culture envelope 2 are in communication with a common plenum. A common medium inlet plenum 470 having medium inlet 405 and a common medium outlet plenum 470' having medium outlet 450 are formed when a number of housing components are assembled together. A common extra-capillary access/inlet distribution plenum 430 having an extra-capillary access/inlet means 420 and a common extra-capillary access/outlet distribution plenum 430' having an extra-capillary access/outlet means 420' are formed when a number of housing components are assembled together. Likewise, a common gas inlet distribution plenum 440 having a gas inlet means 485 and a common gas outlet distribution plenum 440' having a gas outlet means 485' are formed when a number of housing components are assembled together (see FIGS. 13 and 15).

Figure 13A:
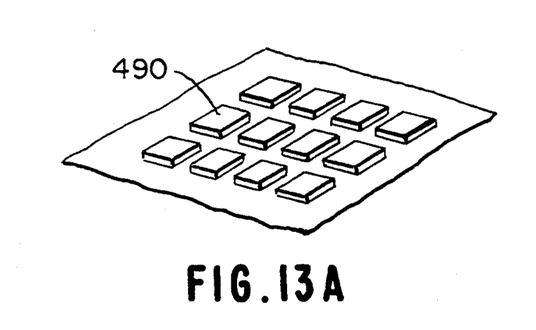
FIG. 13A is a fragmentary perspective view showing a distribution pattern for creating gassing plenums.

In this embodiment, the gassing plenums are created by forming a distribution pattern 490 in the rigid plates, thus eliminating the plastic mesh that is used for gas distribution purposes in the other embodiments. See FIG. 13A for an example of the distribution pattern.

The membrane sheets 30 and 30' are preferably made of a porous hydrophobic material such as medical-grade silicone, micro-porous polyethylene, polysulfone, polycarbonate or polyethylene which is permeable to gases such as air, oxygen and carbon dioxide but impermeable to cells and liquids. The porous membranes generally have a pore size in the range from about 0.02 to 0.4 microns. A preferred material is medical-grade silicone because it does not require additional chemical or physical modifications of its surface to permit the effective attachment of cells thereto and provides for optimally efficient gas exchange between the cell culturing space 75 and the external environment. A particularly preferred material is a fabric-reinforced polymethylsiloxane produced by SciMed Life Systems of Minneapolis, Minn. and by Dow Corning of Midland, Mich. under the name "SILASTIC". Membranes 30 and 30' should also be constructed to be as thin as possible to minimize their resistance to gas diffusion. For example, when silicone is used as the membrane material, a suitable thickness is about 0.125 mm. A preferred thickness of the membrane material is in the range of from about 0.1 mm to 0.250 mm. The above-mentioned hydrophobic materials are also advantageous in that they do not allow water films to form on their surface which increases resistance to gas diffusion.

In this invention, nutrient media is delivered to and water-soluble waste products are removed from the cell culturing space by the plurality of hollow fibers or capillaries 40 having liquid permeable walls, which are disposed within the envelope and whose open ends extend outwardly from between the sealed lateral edges of the envelope such that the capillaries communicate with the cell culturing space 75 only through the walls of the capillaries. The capillaries can be disposed in the envelope substantially equally spaced from and parallel to each other. The distance between the capillaries is generally from about 100 microns to about 1000 microns; the preferred distance is from about 200 microns to about 500 microns. A distance of less than 100 microns is difficult from a manufacturing point of view and does not allow adequate space for cell growth. Spacing of more than 1000 microns tends to cause nutrient gradients to develop in the cell culturing space which, as discussed above, results in less than optimal cell and/or cell product yield. The capillaries can be produced from any suitable material which is non-toxic to cells and which can be spun into fibers which form a semi-porous, hydrophilic, and selectively permeable membrane wall. Examples include cellulose acetate, anisotropic polysulfone, polyethersulfone, saponified cellulose ester, nylon, polyacrylonitrile and acrylic copolymers A preferred material is "CUPROPHAN", a regenerated cellulose acetate manufactured by Enka AG, Wuppertal, Germany. The capillaries 40 transport fresh nutrient media containing glucose, amino acids, vitamins and other essential nutrients necessary for specific cell metabolism requirements to the cells. The media diffuses through the capillary walls into the cell culturing space 75. Cellular waste products diffuse from the cell culturing space 75 into the capillaries 40 and are carried away by the media flowing therethrough. The external diameter of the capillaries 40 is generally in the range from about 60 to 400 microns, preferably from about 210 microns to 300 microns; the internal diameter is generally from about 100 to 300 microns, preferably from about 200 microns to about 250 microns. By varying the placement and/or size of the hollow-fiber capillaries, capillary surface area to cell culture envelope volume ratios of 10 to 100 $cm^2$ per ml may be achieved, with 40:1 to 80:1 being preferred.

Access into the cell culturing space 75 for both the delivery of cells and the removal of cells and/or cell products is provided by entry and exit tubes 20 and 20' respectively Tube 20 is disposed between the first longitudinal edges of the membranes 30 and 30' of the cell culturing envelope 2 and projects into the cell culturing space 75 such that a first end portion of the tube communicates with the cell culturing space 75 and a second end portion of the tube communicates with, for example, a cell delivery means (not shown). Tube 20' is disposed between the second longitudinal edges of the membranes 30 and 30' of the envelope 2 opposite the edges which tube 20 is disposed such that tube 20' projects into the cell culturing space 75 whereby a first end portion of the tube communicates with the cell culturing space 75 and a second end portion of the tube communicates with, for example, a cell and/or cell product collecting means. The entry and exit tubes may be constructed of a flexible biocompatible material such as silicone rubber, polyethylene or polyurethane. A preferred material is silicone rubber. The internal diameter of the tubes should be sufficiently large to allow for adequate cell inoculation into the cell culturing space 75 and the removal of cells and/or cell products therefrom. A suitable internal diameter is generally in the range from about 1.5 mm to about 9.5 mm. The external diameter of the tubes is selected to facilitate bonding or sealing of the tubes 20 and 20' between the longitudinal edges of membranes 30 and 30' which comprise envelope 2. A preferred external diameter is about 3 mm to about 13 mm. Tubes 20 and 20' extend far enough into the cell culturing space 75 merely to provide for adequate cell inoculation and cell and/or cell product harvesting, respectively. Although not shown in the figures, more than one of each of tubes 20 and 20' may be appropriately disposed in the envelope 2.

Any of the embodiments hereinbefore described can be modified in the following way.

To increase the amount of surface area in the cell culturing space for the cells to attach, any positively charged non-toxic particles of from about 200 to 400 microns in diameter such as microcarriers, reticulated polyurethane foam or silica particles can be added to the cell culturing space and enclosed therein upon assembly of the envelope.

A wide variety of different types of animal cells can be cultured in the device of this invention including, for example, amphibian, mammalian and avian cells, particularly mammalian cells. Examples thereof include human lung fibroblast cells, Rhesus monkey kidney cells, vero cells, MDCK cells, Chinese hamster ovary cells, chick fibroblast cells, mouse embryo fibroblast cells and baby hamster kidney cells. Bacterial cells, insect cells, and plant cells can also be cultured therein but this invention is particularly applicable to culture of animal cells as listed above.

The device is also adapted to be used with any conventional nutrient media such as Eagle's basal medium Dulbecco's modified minimum essential medium (MEM) and Earle's or Hank's balanced salt solutions fortified with appropriate nutrients, fetal calf sera, and other materials.

By providing a gas such as oxygen to the cells in the manner described according to the present invention, cells can be grown more economically and cells and/or cell products can be produced in higher yields because the rate at which oxygen is delivered to the cells is greatly increased over what it is in prior art devices. For example, aqueous nutrient media equilibrated with air can carry only 4.5 ml of oxygen per liter of 37° C. and 760 mm Hg pressure while air under the same conditions can carry 209 ml of oxygen per liter. Thus, at least 46 (209/4.5) times more oxygen is available from a liter of air than a liter of water. Moreover, since a gas such as air is less viscous than water, at any given pressure, a greater amount of air per unit time can be delivered to the cell culturing device, thus maintaining a high oxygen gradient. Therefore, in the present invention, the increase in cells and/or cell product can be as much as 10 to 46 times the yield obtained in conventional devices. Also, the fluid flow rate of the non-aerated media can be decreased to be in the order of from 100 to 1000 ml of media per hour per square meter of cell culturing device. It is noted that existing cell culturing devices operate in the order of 500 ml of media per minute per square meter of device in order to supply the amount of oxygen necessary for cell growth. This reduction in flow rate and the commensurate reduction in internal pressure facilitate industrial scale-up.

Although the present invention has been described in detail and with reference to specific embodiments, thereof, it will be apparent to one skilled in the art that changes may be made in form and detail without departing from the spirit and scope of the invention.

What is claimed is:

1. A cell culture device comprising:
   (a) at least one envelope having first and second external surfaces each having first and second lateral and longitudinal edges, wherein the envelope comprises a first, substantially flat membrane sheet sealed to a second, substantially flat membrane sheet along said first and second lateral and longitudinal edges, respectively, to define a cell culturing space therebetween, said first and second membrane sheets being porous and substantially permeable to gasses, but substantially impermeable to cells and liquids;
   (b) a first delivery means for delivering nutrient media to the cell culturing space;
   (c) a second delivery means for delivering cells to the cell culturing space;
   (d) a third delivery means for delivering a gas to said external surfaces of said at least one envelope;
   (e) a first removal means for removing liquid metabolic waste products from the cell culturing space;
   (f) a second removal means for removing cells and/or cell products from the cell culturing space;
   (g) a third removal means for removing gaseous waste products from said external surfaces of said at least one envelope; and
   (h) an upper rigid plate and a lower rigid plate for retaining said envelope, said upper and lower rigid plates having cavities for accommodating said envelope when said upper and lower rigid plates are placed together, wherein said upper rigid plate and said lower rigid plate physically restrain said first and second membrane sheets so as to control said cell culturing space to a distance in a range of 225 to 1000 microns;
   wherein said first delivery means and said first removal means comprise a plurality of capillaries having liquid permeable walls disposed within said envelope and open ends extending outwardly from between said sealed lateral edges of said envelope such that said capillaries communicate with said cell culturing space only through the walls of said capillaries, said capillaries being disposed substantially equally spaced and substantially parallel to each other at a distance of from about 100 microns to about 1000 microns.

2. A cell culture device according to claim 1, wherein said membrane sheets have a pore size of from about 0.02 to 0.4 microns.

3. A cell culture device according to claim 1, wherein each of said membrane sheets comprises medical-grade silicone.

4. A cell culture device according to claim 3, wherein each of said membrane sheets has a thickness of from about 0.125 mm to 0.250 mm.

5. A cell culture device according to claim 1, wherein said second delivery means comprises at least one tube means disposed between said first longitudinal edges of said envelope and projecting into said cell culturing space such that a first end portion of said tube means communicates with said cell culturing space and a second end portion of said tube means communicates with a cell delivery means.

6. A cell culture device according to claim 1, wherein said second removal means comprises at least one tube means disposed between said second longitudinal edges of said envelope, and which projects into said cell culturing space such that a first end portion of said tube means communicates with a cell and/or cell products collecting means.

7. A cell culture device according to claim 1, wherein a mesh is placed atop at least one membrane sheet of said at least one envelope.

8. A cell culture device according to claim 7, wherein said mesh comprises a non-woven plastic screen.

9. A cell culture device according to claim 1, wherein a plurality of said envelopes are disposed between said upper and lower rigid plates.

10. A cell culture device according to claim 9, further comprising a plurality of intermediate plates disposed between said upper and lower rigid plates, so that each of said envelopes is retained between a corresponding pair of plates.

11. A cell culture device according to claim 10, wherein said upper and lower rigid plates and said intermediate plates share a common inlet plenum and a common outlet plenum, said first delivery means of each of said envelopes communicating with said common inlet plenum, and said first removal means of each of said envelopes communicating with said common outlet plenum.

12. A cell culture device according to claim 9, wherein said upper and lower rigid plates are formed with a distribution pattern for distributing gas to the cell culturing space of each envelope.

13. A cell culture device according to claim 10, wherein said intermediate plates are formed with a distribution pattern for distributing gas to the cell culturing space of each envelope.

14. A cell culture device according to claim 10, wherein said intermediate plates are formed with a distribution pattern for distributing gas to the cell culturing space of each envelope, said distribution pattern comprising a plurality of raised portions formed in an array on said intermediate plates.

* * * * *